(12) United States Patent
Bobo, Jr. et al.

(10) Patent No.: US 9,788,946 B2
(45) Date of Patent: Oct. 17, 2017

(54) DEVICES FOR REMODELING A VALVE ANNULUS AND VENTRICLE

(71) Applicant: Edwards Lifesciences Corporation, Irvine, CA (US)

(72) Inventors: Donald E. Bobo, Jr., Santa Ana, CA (US); Assaf Bash, Benyamina-Givat Ada (IL); Louis A. Campbell, Santa Ana, CA (US); Alison S. Curtis, Irvine, CA (US); Tak G. Cheung, Irvine, CA (US); John F. Migliazza, Belmont Shores, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 117 days.

(21) Appl. No.: 14/827,216

(22) Filed: Aug. 14, 2015

(65) Prior Publication Data

US 2015/0351909 A1   Dec. 10, 2015

Related U.S. Application Data

(62) Division of application No. 13/019,506, filed on Feb. 2, 2011, now Pat. No. 9,107,749.

(60) Provisional application No. 61/301,082, filed on Feb. 3, 2010.

(51) Int. Cl.
*A61F 2/24* (2006.01)
*A61B 5/107* (2006.01)
*A61B 6/00* (2006.01)

(52) U.S. Cl.
CPC .......... *A61F 2/2445* (2013.01); *A61F 2/2487* (2013.01); *A61B 5/1076* (2013.01); *A61B 6/503* (2013.01); *A61F 2/2457* (2013.01); *A61F 2220/0008* (2013.01); *A61F 2250/0004* (2013.01); *A61F 2250/0007* (2013.01); *A61F 2250/0012* (2013.01)

(58) Field of Classification Search
CPC .... A61F 2/2445; A61F 2/2466; A61F 2/2442; A61F 2/2418; A61F 2/2454
See application file for complete search history.

(56) References Cited

U.S. PATENT DOCUMENTS

| 2007/0016287 A1* | 1/2007 | Cartledge | A61F 2/2448 623/2.11 |
| 2010/0063586 A1* | 3/2010 | Hasenkam | A61B 17/0401 623/2.37 |
| 2013/0116780 A1* | 5/2013 | Miller | A61F 2/2445 623/2.36 |

* cited by examiner

*Primary Examiner* — Thomas J Sweet
*Assistant Examiner* — Tiffany Shipmon
(74) *Attorney, Agent, or Firm* — Guy L. Cumberbatch; Pui Tong Ho

(57) ABSTRACT

Devices and related methods of use are provided for improving heart function. In one embodiment of the present disclosure, a device includes a ring-like structure configured to be secured to a heart valve; at least one elongate member extending from the ring-like structure, wherein an end of the elongate member is configured to be secured to heart geometry other than a heart valve; and an adjustment mechanism for simultaneously altering a dimension of the ring-like structure and a length of the elongate member.

20 Claims, 12 Drawing Sheets

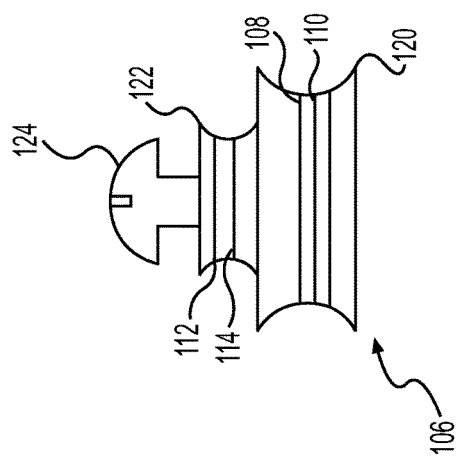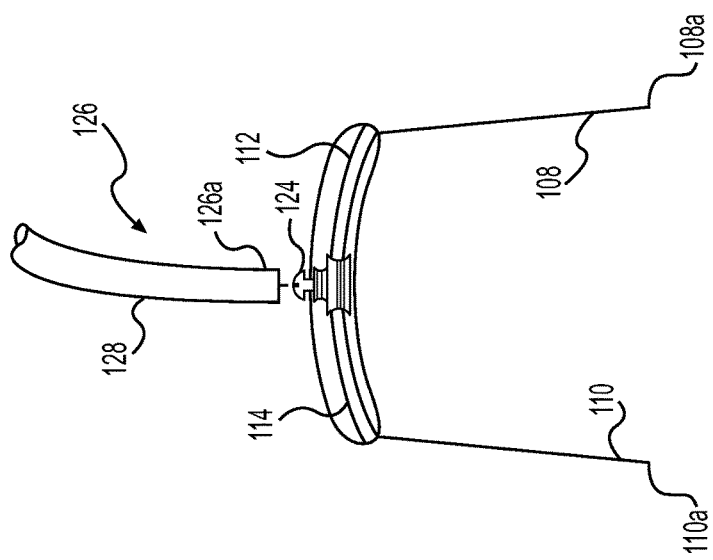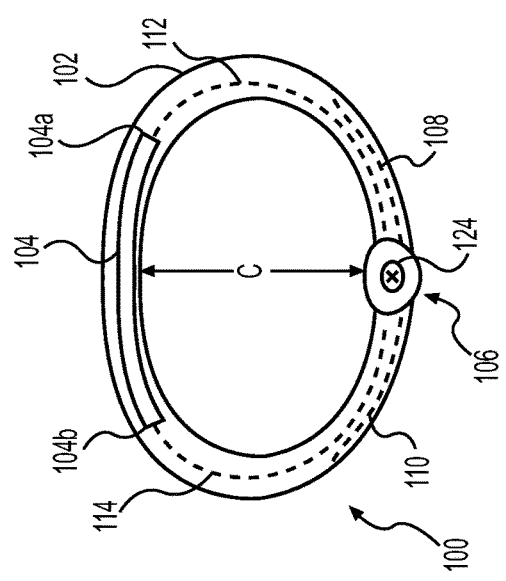

DEVICES FOR REMODELING A VALVE ANNULUS AND VENTRICLE

CROSS-REFERENCE TO RELATED APPLICATIONS

This application is a divisional of U.S. patent application Ser. No. 13/019,506, filed Feb. 3, 2011, now issued as U.S. Pat. No. 9,107,749, which claims the benefit of U.S. Patent Application No. 61/301,082, filed Feb. 3, 2010, the disclosures all of which are hereby expressly incorporated by reference.

FIELD OF THE INVENTION

Embodiments of this disclosure relate generally to medical devices and procedures. In particular, embodiments of the instant disclosure relate to devices and methods for improving heart function, restoring the geometry of ischemically or otherwise damaged heart chambers, and/or treating heart valves, including, but not limited to, a mitral or tricuspid valve of a heart.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, each having flexible flow-occluding leaflets mounted to a surrounding annulus comprising dense fibrous rings that attach either directly or indirectly to the atrial and ventricular muscle fibers.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood or regurgitation through the valve when the leaflets are supposed to coapt together to prevent regurgitation. Valve disease can be severely debilitating and even fatal if left untreated.

As will be explained in greater detail below, the atrioventricular heart valves (i.e., the tricuspid and mitral valves) are located in the center of the heart between the atria and the ventricles of the heart, and play important roles in maintaining forward flow of blood. Atrioventricular valve dysfunction is also commonly known as "regurgitation" and affects well over one million people globally.

Although valve regurgitation often occurs due to the dilatation of the valve annulus, mitral and tricuspid valve function and competency frequently depend on the fine geometric and functional integrity of the valve's supporting structures, such as, for example, the associated subvalvular apparatus. The subvalvular apparatus of these heart valves include, among other things, the associated chordae tendinae and papillary muscles. Indeed, the underlying cause of atrioventricular valve dysfunction is sometimes considered to be a dilatation of the associated ventricular chamber (also known as ventricular remodeling), which results in displacement and tethering of the ventricle's papillary muscles. Displacement of these cardiac muscular prominences hampers correct closure of the associated atrioventricular valve during systole and causes valvular insufficiency.

The anatomic structure of the mitral valve apparatus is particularly complex and consists of several components, each of which can be affected by a variety of diseases resulting in regurgitation. In so-called functional mitral valve regurgitation, the valve is structurally normal and the regurgitation results from failure of the leaflets to coapt. A slow progression of symptoms is typical for this valve disease and often ends in irreversible left ventricular dysfunction.

Another common problem is congestive heart failure or CHF. CHF is a family of related conditions defined by failure of the heart to pump blood efficiently. With over one million new cases occurring each year, CHF is considered to be one of the fastest-growing cardiovascular diseases in the world. And, if left untreated, CHF may result in severe lifestyle restrictions and ultimately death. One of the causes of CHF and a very common contributor to the harmful effects of CHF is a dysfunctional atrioventricular heart valve, such as, for example, the mitral valve.

Thus, what is needed are methods and devices for treating ventricular remodeling and atrioventricular valve regurgitation by addressing the geometric distortion of not only the valve's annulus, but also the supporting structures of the valve.

Additionally, it would be desirable if such a technique could address ventricular remodeling and atrioventricular regurgitation without necessarily requiring cardiopulmonary bypass, the need for which frequently influences surgeons not to repair valves, particularly in patients who are more seriously ill and could benefit most from heart valve repair, but are at greatest risk from prolonged and/or repeated bypass.

Further, because damage to heart geometry may be progressive, initial success in reducing regurgitation and/or ventricular remodeling is often followed by its recurrence. It would therefore be desirable to employ approaches to addressing these conditions that are adjustable over time.

SUMMARY OF THE INVENTION

Embodiments of the present disclosure provide devices and methods for treating a heart.

An aspect of the present disclosure may include a device for treating a heart. The device may include a ring-like structure configured to be secured to a heart valve and at least one elongate member extending from the ring-like structure, wherein an end of the elongate member may be configured to be secured to heart geometry other than a heart valve. The device may further include an adjustment mechanism for simultaneously altering a dimension of the ring-like structure and a length of the elongate member.

Various embodiments of the disclosure may include one or more of the following aspects: the ring-like structure may include an annuloplasty ring; the heart valve may include one of a mitral valve and a tricuspid valve; the heart geometry other than a heart valve may include a papillary muscle; the heart geometry other than a heart valve may include a heart wall; altering a dimension of the ring-like structure may include altering a shape of the ring-like structure; adjusting a length of the elongate member may include adjusting a tension of the elongate member; the at least one elongate member may include a plurality of elongate members; the adjustment mechanism may include a component configured for rotation; the component may include a pulley; the component may include a screw; and the ring-like structure may include a stiffening member.

Another aspect of the present disclosure may include a method of treating a heart valve. The method may include implanting a device within a heart, wherein the device includes a ring-like structure configured to be secured to the heart valve, at least one elongate member extending from the ring-like structure, wherein an end of the elongate member may be configured to be secured to heart geometry other than the heart valve, an adjustment mechanism for altering a dimension of the ring-like structure and a length of the elongate member. The method may further include altering the dimension of the ring-like structure and altering the length of the elongate member.

Various embodiments of the disclosure may include one or more of the following aspects: the method may further include the step of monitoring a function of the heart valve; the steps of altering the dimension of the ring-like structure and altering the length of the elongate member may be performed while the heart is beating; the heart valve may be one of a mitral valve and a tricuspid valve; the heart geometry other than a heart valve may include a papillary muscle; the heart geometry other than a heart valve may include a heart wall; the steps of altering the dimension of the ring-like structure and altering the length of the elongate member may be performed simultaneously; the ring-like structure may include an annuloplasty ring; the at least one elongate member may include a plurality of elongate members; the step of altering the dimension of the ring-like structure and the step of altering the length of the elongate member may occur simultaneously by rotating a component of the adjustment mechanism; the component may include a pulley; and the component may include a screw.

A further aspect of the present disclosure may include a method of treating a heart. The method may include measuring a distance between a mitral-aortic intervalvular fibrosa and a papillary muscle of a heart, measuring a diameter of a heart valve of the heart, and using a predictive model to calculate a change required in the distance between the mitral-aortic intervalvular fibrosa and the papillary muscle of the heart to cause a desired change in the diameter of the heart valve.

Various embodiments of the disclosure may include one or more of the following aspects: the papillary muscle may include a posterior papillary muscle; the heart valve may be one of a tricuspid valve and a mitral valve; the predictive model may be a mathematical function; and the predictive model may be determined by measuring a distance between a mitral-aortic intervalvular fibrosa and a papillary muscle and measuring a diameter of a heart valve, for a plurality of hearts.

Another aspect of the present disclosure may include a method of treating an atrioventricular heart valve. The method may include implanting a device within a heart chamber, wherein the device includes an annuloplasty ring configured to be secured to the atrioventricular heart valve; a plurality of elongate members extending from the annuloplasty ring, wherein an end of each of the elongate members is configured to be secured to one of a heart wall and a papillary muscle; and an adjustment mechanism for simultaneously altering a diameter of the annuloplasty ring and exerting a pulling force on at least one of the plurality of elongate members. The method may further include altering the diameter of the annuloplasty ring and exerting a pulling force on the plurality of elongate members so as to alter a positioning of one of the heart wall and the papillary muscle, during the step of altering the diameter of the annuloplasty ring.

Various embodiments of the disclosure may include one or more of the following aspects: the step of altering the diameter of the annuloplasty ring and the step of exerting a pulling force on the plurality of elongate members may occur simultaneously through adjusting the adjustment mechanism; the method may further include the step of monitoring a function of the atrioventricular heart valve; the atrioventricular heart valve may include a mitral valve; adjusting the adjustment mechanism may include rotating a component of the adjustment mechanism; the component may include a pulley; and the component may include a screw.

A further aspect of the present disclosure may include a method of determining a predictive model for heart valve treatment. The method may include compiling measurements of a distance between a mitral-aortic intervalvular fibrosa and a papillary muscle for a plurality of hearts, compiling measurements of a diameter of a heart valve associated with the papillary muscle for the plurality of hearts, and evaluating the measurements to determine the predictive model.

In one embodiment, the step of evaluating the measurements may include performing a regression analysis calculation on the measurements.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the invention and, together with the description, serve to explain the principles of the invention.

FIGS. 5A-5D depict schematic views of a heart treatment device, in accordance with an embodiment of the present disclosure.

DETAILED DESCRIPTION OF PREFERRED EMBODIMENTS

The various aspects of the devices and methods described herein generally pertain to devices and methods for treating, including, for example, ventricular dilatation, valve incompetencies, including mitral valve and tricuspid valve regurgitation, and other similar heart failure conditions. Implanting one or more of the disclosed devices operates to, among other things, assist in the apposition of heart valve leaflets to improve valve function and reverse distortion of heart geometry associated with ventricular remodeling.

In addition, these devices may either be placed in conjunction with other devices, or may themselves function to alter the shape or geometry of the heart, locally and/or globally, and thereby further increase the heart's efficiency. That is, the heart experiences an increased pumping efficiency through an alteration in its shape or geometry and concomitant reduction in stress on the heart walls, and through an improvement in valve function.

Although the methods and devices are discussed hereinafter in connection with their use in the left ventricle and for the mitral valve of the heart, these methods and devices may be used in other chambers and for other valves of the heart for similar purposes, as would be readily apparent to those of ordinary skill in the art. The left ventricle and the mitral valve have been selected for illustrative purposes because a large number of the disorders occur in the left ventricle and in connection with the mitral valve.

The following detailed description of exemplary embodiments of the present disclosure is made with reference to the drawings, in which similar elements in different drawings may be numbered the same. The drawings, which are not necessarily to scale, depict illustrative embodiments and are not intended to limit the scope of the invention.

Figure 1:
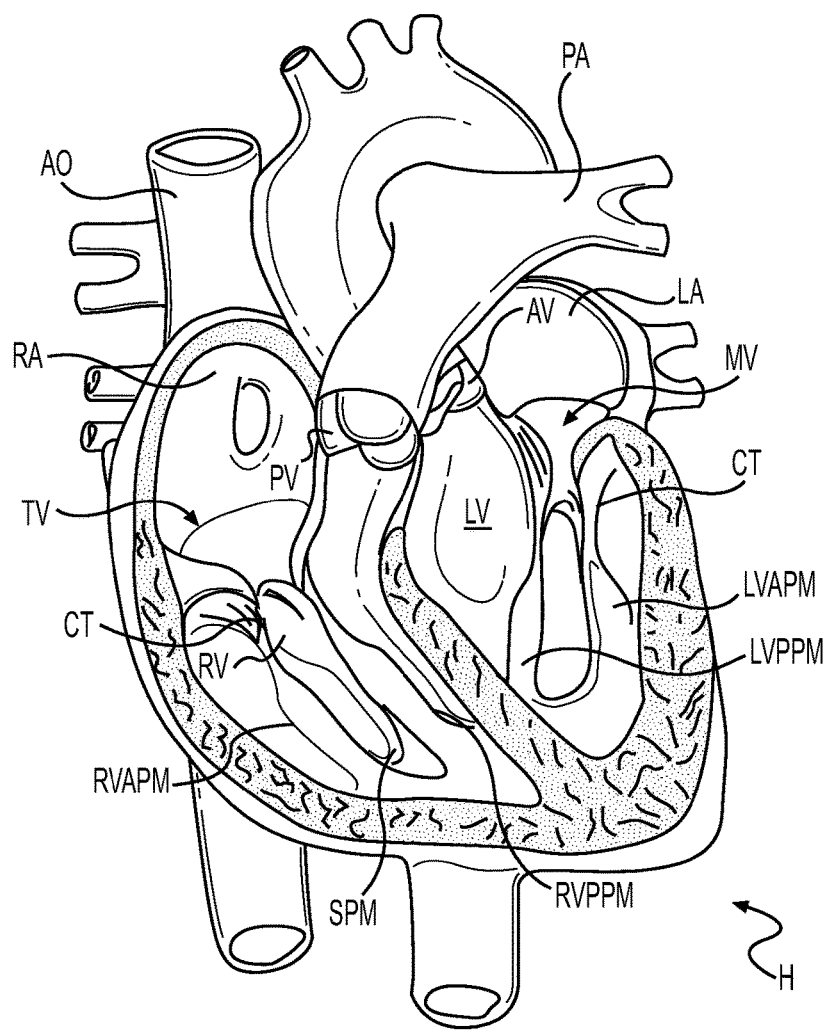
FIG. 1 is a cross-sectional view of a human heart.

Turning to FIG. 1, the human heart H includes four chambers. These chambers are the left atrium LA, the left ventricle LV, the right ventricle RV, and the right atrium RA. In its path through the heart, circulating blood encounters four valves. The valve on the right side that separates the right atrium RA from the right ventricle RV has three cusps or leaflets and is called the tricuspid valve TV. The tricuspid valve TV is typically closed during ventricular contraction (i.e., systole) and opens during ventricular expansion (i.e., diastole).

The pulmonary valve PV separates the right ventricle RV from the pulmonary artery PA. The pulmonary valve PV is configured to open during systole so that blood may be pumped towards the lungs, and close during diastole to prevent blood from leaking back into the heart from the pulmonary artery PA. The pulmonary valve PV has three cusps, each one resembling a crescent, and is frequently known as a semilunar valve.

The two-cusped mitral valve MV separates the left atrium LA from the left ventricle LV. The mitral valve MV is configured to open during diastole so that blood in the left atrium LA can pour into the left ventricle LV, and close during diastole to prevent blood from leaking back into the left atrium LA.

The fourth valve is the aortic valve AV and it separates the left ventricle LV from the aorta AO. The aortic valve AV is configured to open during systole to allow blood leaving the left ventricle LV to enter the aorta AO, and close during diastole to prevent blood from leaking back into the left ventricle LV.

As alluded to above, the mitral and tricuspid valves, also called atrioventricular valves, prevent regurgitation of blood from the ventricles into the atria when the ventricles contract. Unlike the passive aortic and pulmonary valves, the mitral and tricuspid valves are considered active valves having two components: one at the annulus level (the leaflets) and the other below (the sub-valvular apparatus). In order to withstand the substantial back pressure and effectively prevent regurgitation of blood into the atria during ventricular contraction, the cusps of the mitral and tricuspid valves are held in place by a plurality of delicate chordae tendinae CT. The chordae tendinae CT serve to anchor the valve cusps to papillary muscles PM (e.g., RVAPM, RVPPM, SPM, LVAPM, LVPPM) in the right and left ventricles RV, LV. As those of ordinary skill in the art will recognize, the papillary muscles PM arise from the lower portions of the interior walls of the left ventricle LV and right ventricle RV. The papillary muscles PM function to limit the movement of the leaflets of the atrioventricular valves. In particular, the papillary muscles contract during portions of the cardiac cycle to tighten the chordae tendinae CT, which in turn prevent inversion of the valves' leaflets.

With continued reference to FIG. 1, the left ventricle LV includes two papillary muscles, the anterior papillary muscle LVAPM and the posterior papillary muscle LVPPM. The right ventricle RV, on the other hand, includes three papillary muscles, the anterior papillary muscle RVAPM, the posterior papillary muscle RVPPM, and the septal papillary muscle SPM.

Figure 2:
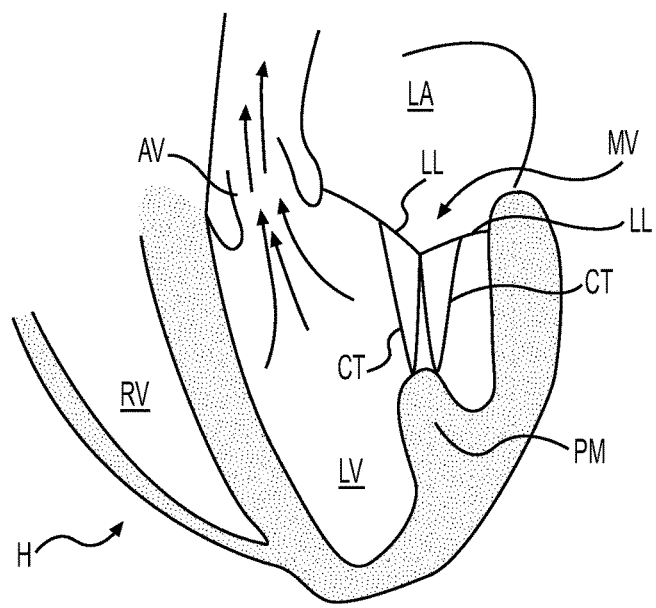
FIG. 2 is a cross-sectional view of a normal human heart during systole.
Figure 3:
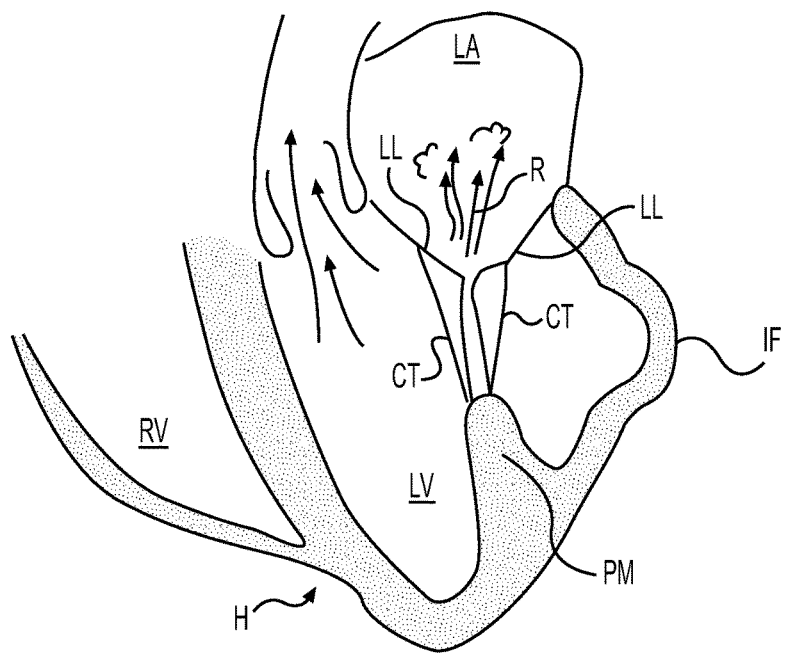
FIG. 3 is a cross-sectional view of a diseased human heart during systole.

Turning now to FIGS. 2 and 3, an example of a cardiac condition that can be treated with embodiments of the present disclosure is briefly discussed to facilitate description of the embodiments disclosed herein. The following discussion is for exemplary purposes only and aspects of the disclosed embodiments may be used to treat any number of cardiovascular conditions and/or disorders, including, but not limited to, ischemic heart disease and cardiomyopathy.

FIG. 2 shows a section through a portion of a normally functioning heart H. More particularly, FIG. 2 shows in schematic form a long-axis section through a left ventricle LV and left atrium LA of a normal heart H during systole. The aortic valve AV is open (the arrows in the vicinity of the aortic valve AV indicating the flow of blood) and the mitral valve MV is closed. As noted above, the mitral valve MV includes two cusps or leaflets LL. As also noted above, the chordae tendinae CT of the left ventricle LV, together with the ventricle's papillary muscles PM (in these views the papillary muscles are collectively represented by a single papillary muscle), ensure that the two leaflets LL of the mitral valve MV interact over a broad coaptation area to ensure a tight mitral valve MV function, so as to prevent blood from reentering the left atrium LA.

In FIG. 3, a section similar to the one shown in FIG. 2 is depicted. In FIG. 3, however, a portion of the posterior left ventricular wall includes an infarction IF. As a consequence of the infarction IF, the papillary muscles PM are displaced outwardly and away from the mitral valve MV. Consequently, the leaflets LL of the mitral valve MV are drawn down and into the ventricle via the chordae tendinae CT. This is known as tethering. Consequently, the mitral valve MV leaks blood to the left atrium LA during systole, as indicated by arrows R. Stated differently, the phenomenon of mitral regurgitation is experienced.

As discussed above, ventricular dilatation may adversely affect the functionality of an associated atrioventricular valve. In particular, as a ventricle's walls dilate outwardly, the papillary muscles associated with the walls are also similarly displaced. The displaced papillary muscles become tethered and prevent the atrioventricular valve from fully closing. As would follow naturally, those of ordinary skill in the art will readily recognize that restoring papillary muscle positioning may have a positive effect on valve functionality and may promote better closure of the valve. As used herein, the term "restoring," with respect to cardiac geometry, refers to moving cardiac geometry towards its normal or preferred positioning and does not necessarily require complete restoration of normal cardiac geometry.

According to one aspect of the present disclosure, therefore, it is believed that a mathematical relationship may exist between the positioning of the papillary muscles and a diameter of the associated atrioventricular valve. For the purposes of discussion only, reference will be made to the left ventricle LV and the associated mitral valve MV to describe the principles of the present disclosure. Those of ordinary skill, however, will readily recognize that the principles of the present disclosure may be applicable to any heart chamber and corresponding heart valve, including, but not limited to, the right ventricle RV and the associated tricuspid valve TV.

Figure 4:
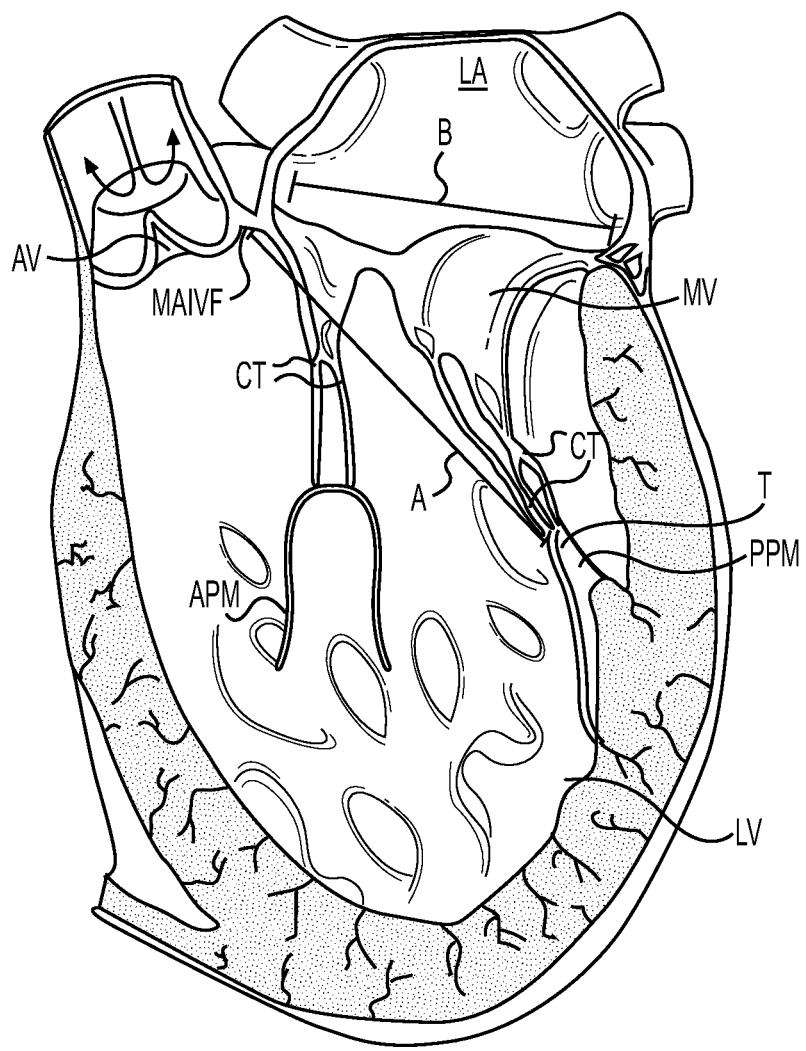
FIG. 4 is a cross-sectional view of a left atrium and left ventricle of a human heart.

Turning now to FIG. 4, there is depicted another cross-sectional view of the left atrium LA and left ventricle LV of a heart H. The mitral valve MV is separated from the aortic valve AV by a fibrous region of the heart known as the mitral-aortic intervalvular fibrosa MAIVF or the mitral-aortic membrane. In accordance with the principles of the present disclosure, it has been found that a direct proportional relationship may exist between a distance A, measured between the mitral-aortic intervalvular fibrosa MAIVF and a tip of one of the anterior papillary muscle LVAPM and the posterior papillary muscle LVPPM of the left ventricle LV, and a diameter B of the annulus of mitral valve MV. Stated differently, it has been found that a diameter B of the annulus of mitral valve MV may be expressed and/or quantified as a mathematical function of distance A. Those of ordinary skill in the art will readily recognize that distance A also may be expressed and/or quantified as a mathematical function of diameter B. In one embodiment, distance A may be measured between the mitral-aortic intervalvular fibrosa MAIVF and a tip T of the posterior papillary muscle LVPPM. In other embodiments, however, distance A may be measured between the mitral-aortic intervalvular fibrosa MAIVF and a tip of the anterior papillary muscle LVAPM.

The principles of the present disclosure, therefore, contemplate a method of calculating the corresponding change in one of distance A and diameter B resulting from a deliberate change to the other of distance A and diameter B. In one embodiment, for example, it may be possible to determine the reduction in diameter B resulting from a reduction in distance A. In particular, it is contemplated that if diameter B and distance A may be known, and it is desired to change diameter B by altering the positioning of the papillary muscles PM, it may be possible to calculate the change in distance A necessary to bring about a desired change to diameter B.

With continued reference to FIG. 4, it may be possible to determine distance A and/or diameter B in a patient's heart by any of the suitable imaging techniques known in the art, including, but not limited to, transesophageal echocardiography, infrared illumination, X-ray, and magnetic resonance imaging. Similarly, it may be possible to monitor the changes to distance A and/or diameter B with the aforementioned imaging techniques.

In accordance with the principles of the present disclosure, the relationship between distance A and diameter B may be determined by any suitable means known in the art. In one embodiment, distance A and diameter B may be determined experimentally or empirically, and the relationship between these two cardiac dimensions may be determined numerically. For example, it is contemplated that the mitral valve annulus diameter B and the distance A between the MVAIF and the tip T of the posterior papillary muscle PPM of a plurality of hearts may be measured and tabulated. The measured data may be then evaluated via, for example, curve fitting or regression analysis, to, among other things, represent the measured data with a predictive model based on mathematical functions, so that the parameter values that most closely match the measured data may be identified. While the measured data may be evaluated by any suitable means known in the art, those of ordinary skill in the art will readily recognize that the data may be evaluated by hand calculations and/or any suitable computer software program known in the art. Once the evaluation yields a predictive model that represents the measured data, the mathematical functions of the model may be used to predict the change in the distance A between the MVAIF and the tip T of the posterior papillary muscle that is likely to result in a desired change to the dimensions (e.g., diameter B) of an annulus of a mitral valve. That is to say, the mathematical functions of the model may be used to calculate the change required in the distance between the MVAIF and the tip of the posterior papillary muscle to yield a desired change in the diameter of the mitral valve annulus. Thus, for a given mitral valve annulus diameter, the change required in the distance between the MVAIF and the tip of the posterior papillary muscle may be calculated by the mathematical functions of the predictive model.

Figure 5D:
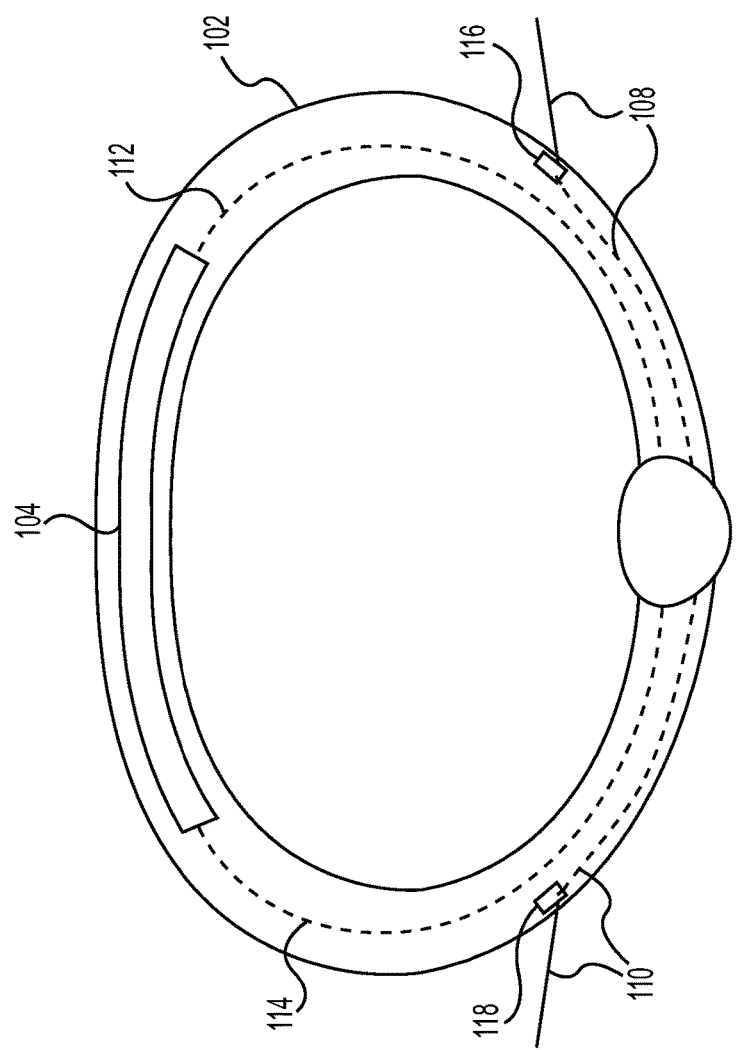
Figure 6:
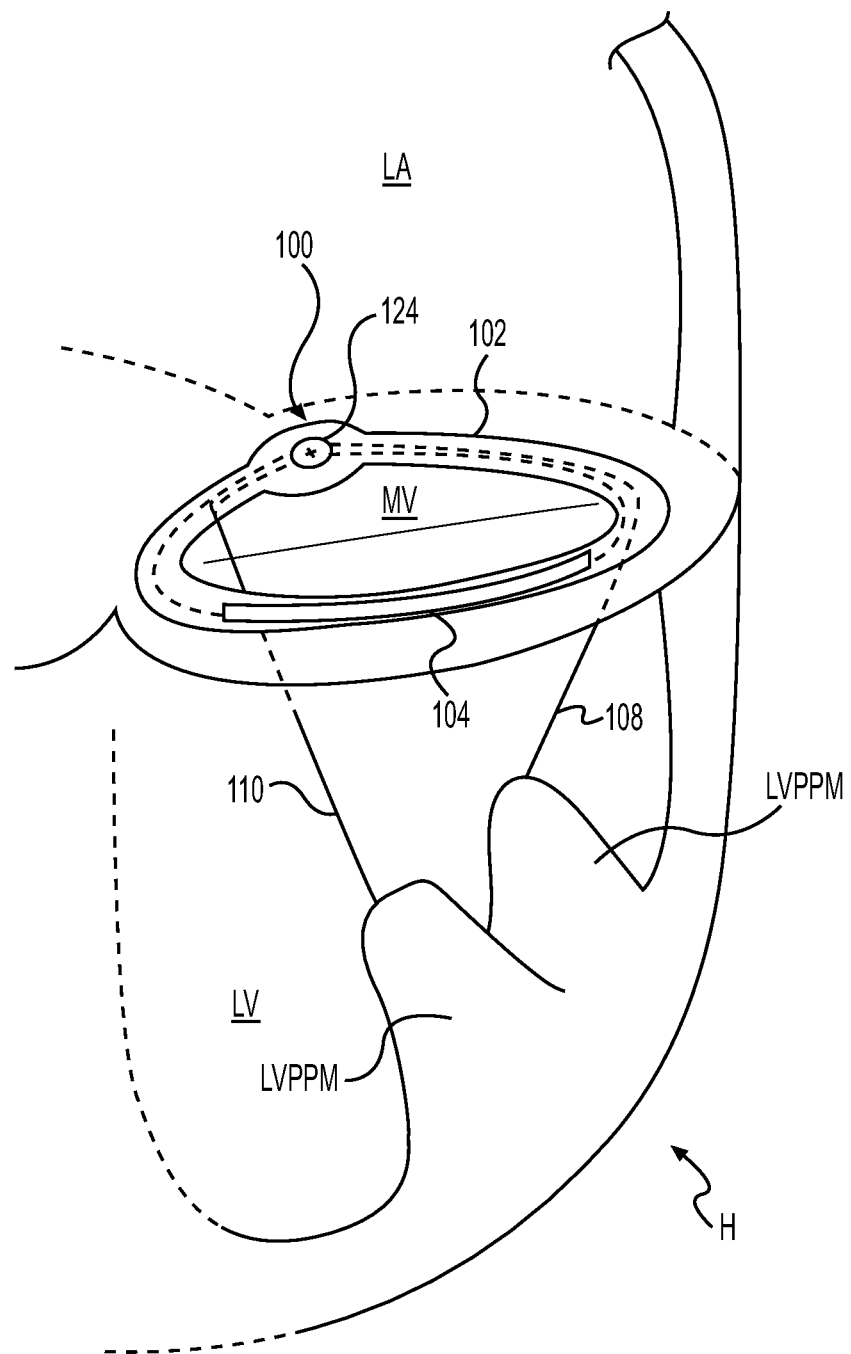
FIG. 6 is a perspective view of an embodiment of the heart treatment device of FIGS. 5A-5D implanted within a patient's heart.

Turning now to FIGS. 5A-5D and 6, there is depicted an embodiment of a heart treatment device 100 in accordance with the principles of the present disclosure. As shown in FIGS. 5A, 5D, and 6, device 100 may include a body 102 having a ring-like structure. Although the depicted embodiments indicate that body 102 may be formed as a closed (or continuous) ring, those of ordinary skill in the art will readily recognize that the heart treatment devices of the present disclosure may include open (or discontinuous) ring-like structures, including, but not limited to, semicircular structures. In accordance with embodiments of the present disclosure, device 100 may be configured to be secured proximate a heart valve, such as, for example, an atrioventricular valve, as will be discussed in greater detail below.

Body 102 may include any suitable shapes, dimensions, and/or geometric configurations known in the art. In one embodiment, body 102 may include a substantially circular shape. In other embodiments, however, body 102 may include a substantially oval or elliptical shape. For example, body 102 may include an annuloplasty ring. In addition, body 102 may be substantially planar (e.g., two dimensional) or nonplanar (e.g., three dimensional). In one embodiment, body 102 may be substantially "saddle-shaped," as depicted in FIG. 5B. In other embodiments, body 102 may include one or more suitable three-dimensional configurations. For example, a posterior portion of body 102 may rise or bow upward from adjacent sides of body 102, as disclosed in U.S. Patent Application Publication No. 2003/0093148, which is entitled Mitral Valve Annuloplasty Ring for Molding Left Ventricle Geometry, the entirety of which is incorporated herein by reference. As a further example, body 102 may have a plurality of portions that may rise or bow upwards so that body 102 may have, for example, a bimodal saddle shape. It is contemplated that such a bimodal saddle-shaped body may be suitable for treatment of a tricuspid valve TV.

Additionally, body 102 may be formed from any suitable biocompatible material known in the art, including, but not limited to, Dacron™, titanium, cobalt chromium, polymers, silicone, nitinol, polyester, and denatured biological material. Furthermore, body 102 may be formed of hallowed stranded cable. Those of ordinary skill in the art will readily recognize that body 102 may include one or more suitable coatings (not shown) known in the art. Such coatings may include, but are not limited to, therapeutic agents. Body 102 may further include a covering, such as, for example, a covering comprised of fabric configured to promote tissue ingrowth. Furthermore, body 102 may include one or more mechanisms to facilitate securing device 100 to an atrioventricular valve. For example, body 102 may include a plurality of openings (not shown) configured to facilitate sewing, stitching, and/or suturing device 100 to an annulus of a heart valve.

In one embodiment, body 102 may be hollow or substantially hollow. For example, body 102 may be constructed as a hollow tube. Body 102 may be constructed by any suitable means known in the art, such as, for example, extrusion or molding. In some embodiments, body 102 may be formed of a coiled wire or spring. In other embodiments, body 102 may be substantially solid. In embodiments where body 102 is substantially solid, body 102 may further include one or more channels disposed within body 102. The channels within body 102 may be configured to receive one or more elongate members, such as, for example, elongate members 108, 110, 112, and 114, which will be discussed in greater detail below. The channels may have any suitable geometric configuration and dimensions. In addition, the channels may be configured to decrease the wear and tear of the elongate members within the channels. For example, the inner surfaces of the channels may be coated with a lubricious agent to reduce the channels' coefficient of friction. Furthermore, body 102 may include any suitable cross-sectional configurations and dimensions. For example, body 102 may include a substantially circular cross-sectional configuration. In some embodiments, body 102 may include one or more differing cross-sectional configurations or dimensions along its length. As will be discussed in greater detail below, one or more dimensions of body 102 and/or a shape of body 102 may be selectively adjustable.

Additionally, body 102 may be substantially rigid or substantially flexible or compressible. In addition, the flexibility or rigidity of body 102 may be selectively adjustable, as discussed in greater detail below. In some embodiments, however, body 102 may include one or more portions of differing rigidity or flexibility. For example, a posterior portion of body 102 may be more or less flexible than an anterior portion of body 102. Differing rigidities or flexibilities may be achieved along body 102 by any suitable means known in the art. For example, portions of body 102 may be made of materials having differing flexibilities or rigidities. In addition, portions of body 102 may be provided with one or more suitable geometric structures and/or features configured to increase or decrease rigidity of those portions, as desired. For example, in order to increase rigidity and decrease flexibility of a portion of body 102, that portion may be provided with one or more supporting structures, which may be internal or external to body 102. As shown in FIGS. 5A and 5D, one embodiment of body 102 may include an elongated stiffening segment 104 disposed within body 102. In embodiments where it is desired to increase the flexibility of a portion of body 102, that portion of body 102 may be provided with, for example, notches (not shown).

Stiffening segment 104 may be made of any suitable material and may have any suitable geometric configuration and/or dimensions. Although the depicted embodiments of stiffening segment 104 indicate that stiffening segment 104 may be made of a one-piece construction, those of ordinary skill in the art will readily recognize that stiffening segment 104 may comprise a plurality of spaced-apart segments. Stiffening segment 104 may be made of any suitable material. In one embodiment, it is contemplated that stiffening segment 104 may be made of a material having a greater rigidity than the material of body 102.

As alluded to above, one or more dimensions of device 100 may be selectively adjustable. For example, a diameter C of body 102 may be adjusted as desired. Although the depicted embodiments indicate that smaller diameter C may be selectively adjusted, those of ordinary skill in the art will recognize that the larger diameter (i.e., the diameter orthogonal to diameter C) of body 102 may be additionally or alternatively adjusted. Further, in embodiments where body 102 includes a three-dimensional configuration, such as, for example, the embodiment depicted in FIG. 5B, a curvature of body 102 may be also selectively adjusted. Embodiments of device 100 therefore may include any suitable configuration or mechanism for selectively adjusting one or more dimensions of body 102.

In one embodiment, body 102 may include one or more strategically disposed magnets (not shown). For example, a plurality of magnets may be disposed within body 102. In these embodiments, the magnets may be configured to adjust a dimension of body 102 when desired. For example, the magnets may exert a force and/or be displaced when an activator magnet (e.g., a magnet having a polarity opposite to the polarity of those disposed in body 102) is disposed proximate to device 100.

In another embodiment, body 102 may be fabricated from a material configured to return to a preset shape or configuration when activated. For example, body 102 may be fabricated from a shape memory material, such as, for example, nitinol. In such embodiments, device 100 may be implanted in a first configuration and selectively adjusted to a second configuration as desired. For example, device 100 may be provided with a component (not shown) designed to keep body 102 in a first configuration. Removal of the component would then allow body 102 to return to a second, preset configuration. The component may be removed in any suitable matter known in the art. For example, the component may be removed by an operator. Alternatively, the component may be made of a bioabsorbable material so that the component is configured to dissolve within the patient's body after a previously determined period of time. In other embodiments, body 102 may be fabricated from a heat-activated material so that body 102 is configured to undergo a geometric change when exposed to heat (e.g., body heat) for a predetermined length of time.

In further embodiments, device 100 may include a mechanical mechanism for exerting a force on body 102 to alter a geometric configuration or dimension of device 100. In one example, adjustment mechanism 106 may include a plurality of elongate members 112, 114. Elongate members 112, 114 may include any suitable geometric configuration.

In addition, elongate members 112, 114 may be made of any suitable material, including, but not limited to, nylon, nickel alloys, and titanium alloys. Elongate members 112, 114 may be disposed within one or more compartments or circumferential channels (not shown) formed along portions of the perimeter of body 102. The compartments or circumferential channels may have any suitable configuration known in the art. In some embodiments, the surfaces of the compartments or circumferential channels may be coated with one or more substances, such as, for example, a lubricious agent, to reduce the wear and tear on elongate members 112, 114 as they move within the compartments or circumferential channels.

In the depicted embodiments, elongate members 112, 114 may extend from adjustment mechanism 106, which will be discussed in greater detail below. As shown in FIG. 5A, for example, elongate members 112, 114 may be connected to stiffening segment 104. For example, elongate member 112 may be connected to a first end 104a of stiffening segment 104, and elongate member 114 may be connected to a second end 104b of stiffening segment 104. Although the depicted embodiments depict two elongate members 112, 114 connected to stiffening member 104, those of ordinary skill in the art will recognize that device 100 may include a greater or lesser number of elongate members extending from adjustment mechanism 106 for connection to stiffening member 104. Elongate members 112, 114 may be connected to stiffening segment 104 by any suitable manner known in the art, including, but not limited to, an adhesive or soldering. In some embodiments, elongate members 112, 114 may be integral to stiffening member 104, and may extend from stiffening member 104 to adjustment mechanism 106. In these embodiments, there may not be a need to connect elongate members 112, 114 to stiffening member 104.

As will be discussed in greater below, the principles of the present invention contemplate adjusting adjustment mechanism 106 to exert a force (e.g., a tensile force) on each of elongate members 112, 114 and, consequently, ends 104a, 104b of stiffening member 104. Adjustment mechanism 106 may exert a force on ends 104a, 104b by, among other things, pulling on elongate members 112, 114. The forces exerted on stiffening member 104 may cause ends 104a, 104b to be pulled towards adjustment mechanism 106, bending stiffening member 104 and causing a reduction in a dimension, such as, for example, a radius of curvature, of stiffening member 104 and body 102. As those of ordinary skill in the art will recognize, pulling on ends 104a, 104b and deforming stiffening member 104 in the above-described manner may deform body 102 in such a manner so as to reduce diameter C. The principles of the present disclosure contemplate utilizing elongate members 112, 114, and adjustment mechanism 106 to not only reduce one or more dimensions of body 102, but also to increase those dimensions as desired. Furthermore, elongate members 112, 114 and adjustment mechanism 106 may be utilized to alter a shape of body 102. In addition, it is contemplated that adjusting a shape or dimension of body 102 may result in similarly adjusting a shape or dimension of, for example, a heart valve annulus to which body 102 may be secured.

With reference to FIGS. 5A, 5B, 5D and 6, device 100 may additionally include elongate members 108, 110. Although the depicted embodiments indicate that device 100 may include two elongate members 108, 110, those of ordinary skill in the art will readily recognize that a greater or lesser number of elongate members may depend from body 102. Like elongate members 112, 114, elongate members 108, 110 also may be disposed in one or more of the above-described compartments or circumferential channels. Each of elongate members 108, 110 may extend from adjustment mechanism 106, and may be configured for attachment to a heart structure, including, but not limited to, a papillary muscle or heart wall. In particular, each of elongate members 108, 110 may extend in opposing directions from adjustment mechanism 106, extend within a portion of body 102, and then extend out of body 102 via openings 116, 118 so that ends 108a, 110a may be connected to a heart structure, including, but not limited to, a papillary muscle or heart wall. In some embodiments, ends 108a, 110a may not be connected to a heart valve.

Openings 116, 118 may include any suitable size or shape configured to permit movement of elongate members 108, 110 therethrough. In some embodiments, openings 116, 118 may be reinforced along a rim or edge of openings 108, 110 in order to increase the resistance to wear and tear caused by elongate members 108, 110 being moved/drawn with respect to openings 116, 118. Alternatively, or in addition, the edges of openings 108, 110 may include any suitable coating known in the art to facilitate movement of elongate members 108, 110 relative to openings 116, 118.

Elongate members 108, 110 may include a unitary or composite structure. In some embodiments, elongate members 108, 110 may include sutures or other biocompatible material, such as, for example, nitinol. In addition, elongate members 108, 110 may be configured to resist elastic deformation so that they do not stretch longitudinally. Notwithstanding the aforementioned, those of ordinary skill in the art will readily recognize that, in some embodiments, elongate members 108, 110 may have some elastic properties, to, for example, minimize the risks of ends 108a, 110a tearing through the heart tissue to which they may be secured.

Exemplary embodiments of each of elongate members 108, 110 may include an inner cable or wire (not shown) to provide, for example, mechanical integrity and an outer covering (not shown) to provide, for example, biocompatibility. The inner cable may include any known, suitable configuration and be made of any suitable material known to those of ordinary skill in the art. By way of example, not limitation, the inner cable of elongate members 108, 110 may have a braided-cable construction such as, for example, a multifilar braided polymeric construction. In general, the filaments forming the inner cable of elongate members 108, 110 may comprise, among other things, high performance fibers. For example, the inner cable may comprise (braided or unbraided) filaments of ultra-high molecular weight polyethylene available under the trade names SPECTRA™ and DYNEEMA™. Alternatively, it is contemplated that the inner cable may include filaments of other known, suitable materials, such as, for example, polyester available under the trade name DACRON™ or liquid crystal polymer available under the trade name VECTRAN™.

The inner cable of elongate members 108, 110, and consequently elongate members 108, 110, may be configured to withstand the cyclical stresses within a heart chamber without breaking or weakening, provide a strong connection to the aforementioned heart structure, minimize damage to internal vascular structure and heart tissue, and minimize the obstruction of blood flow within the heart chambers.

As mentioned above, the inner cable of elongate members 108, 110 may be surrounded by an outer covering, which may provide properties that facilitate sustained implantation in a patient's heart. Specifically, because elongate members 108, 110 may be exposed to blood as they reside within a heart chamber, the outer covering may provide, among other things, resistance to thrombus formation. Furthermore, because of the relative motion that occurs between the heart H and certain portions of elongate members 108, 110 passing through the heart structure, the outer covering may be configured to allow for tissue ingrowth to establish a relatively firm bond between elongate members 108, 110 and the heart structure through which elongate members 108, 110 pass. Such tissue ingrowth may result in reducing the relative motion between elongate members 108, 110 and the heart structure they contact, and potential irritation of the heart.

The outer covering surrounding the inner cable of elongate members 108, 110 may include any known, suitable configuration and be made of any suitable material known to those having ordinary skill in the art. For example, in one embodiment, the outer covering may include a braided tube (not shown) of any suitable configuration. In other embodiments, the outer covering may include a removable sleeve made of porous expanded polytetrafluoroethylene (ePTFE). In some embodiments, the ePTFE material may be preferred because it is biostable and resists degradation and/or corrosion in the body.

As alluded to above, the ePTFE material of the outer covering may be configured to promote tissue ingrowth. For example, the ePTFE material of the outer covering may have an internodal distance of between approximately 20 and approximately 70 microns, such as, for example, approximately 45 microns. Such internodal distance configuration may serve to facilitate cellular infiltration, which in turn may result in secure ingrowth of the adjacent heart structure tissue so as to create a tissue surface on the surfaces of elongate members 108, 110 contacting heart structure. The ePTFE material, particularly having the internodal spacing discussed above, may be preferred because it also possesses a high resistance to thrombus formation and is capable of withstanding the cyclic bending environment associated with a beating heart. Although ePTFE has been described as a suitable material for the outer covering of the elongate member, other known, suitable materials exhibiting similar characteristics also may be used. In embodiments where the outer covering may be configured as a braided tube, ePTFE may be employed as a coating on the tube.

Additionally, since elongate members 108, 110 may be implanted within a heart in a number of ways, such as, for example, by means of an imaging device; portions of elongate members 108, 110 may include radiopaque material and/or sonoreflective markers to facilitate fluoroscopic visualization during implantation procedures.

As briefly noted above, ends 108a, 110a may be secured to heart structure, such as, for example, a papillary muscle and/or a heart wall. As shown in, for example, FIG. 6, elongate member 108 may be secured to a posterior papillary muscle LVPPM of the left ventricle, and elongate member 110 may be secured to an anterior papillary muscle LVAPM of the left ventricle. Although not depicted, those of ordinary skill in the art will readily recognize that, in at least some embodiments, elongate members 108, 110 may traverse the ventricle so that elongate member 108 may be secured to an anterior papillary muscle LVAPM or heart wall and elongate member 110 may be secured to a posterior papillary muscle LVPPM or heart wall. Furthermore, the principles of the present disclosure contemplate a single elongate member extending from body 102, extending through one of the anterior papillary muscle LVAPM and the posterior papillary muscle LVPPM, and being secured to the other of the anterior papillary muscle LVAPM and the posterior papillary muscle LVPPM. In such embodiments, pulling on the single elongate member may alter the positioning of both papillary muscles LVAPM and RVAPM.

Figure 7:
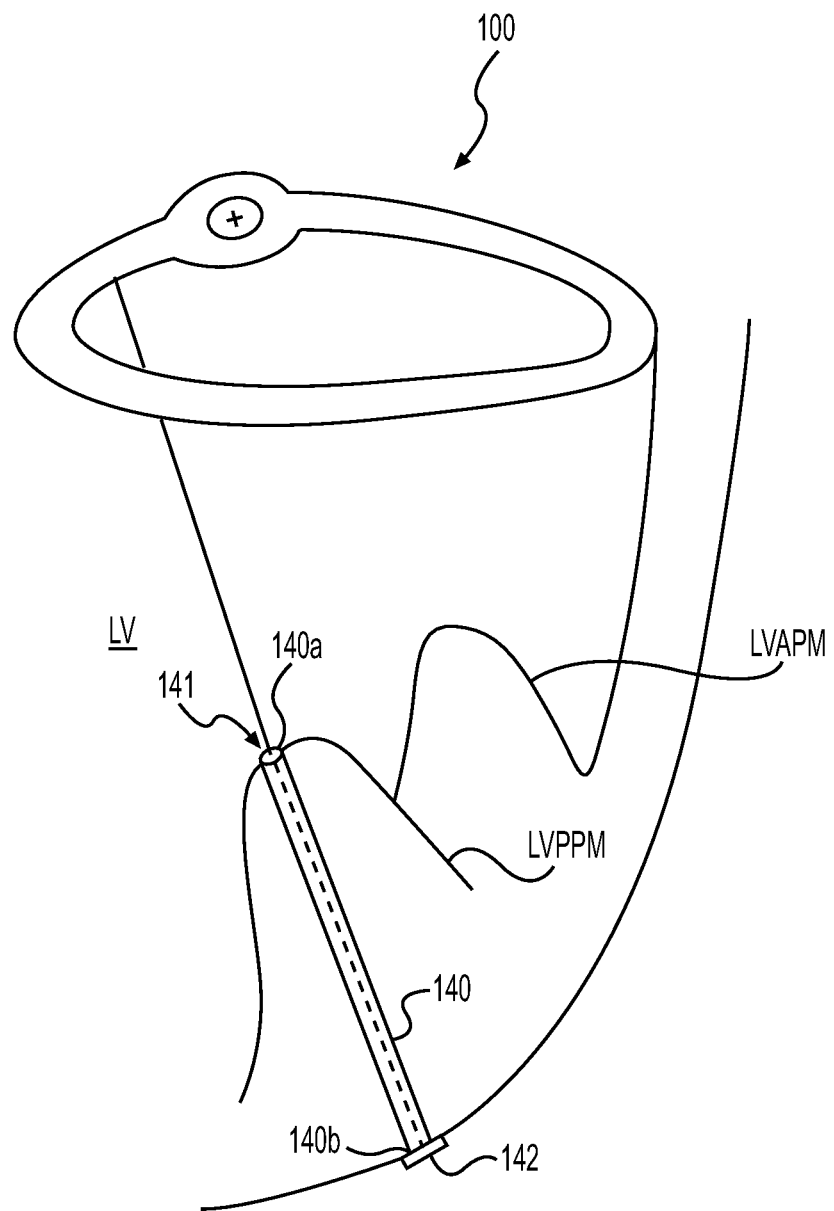
FIG. 7 is another perspective view of an embodiment of the heart treatment device of FIGS. 5A-5D implanted within a patient's heart.

As alluded to above, ends 108a, 110a of elongate members 108, 110 may be secured to papillary muscles of a ventricle, or may be secured transmurally to a heart wall, such as, for example, an external heart wall, as shown in FIG. 7. In embodiments where ends 108a, 110a of elongate members 108, 110 are secured to an external heart wall, device 100 may further include one or more tubular members 140 for providing a channel through heart structure, such as, for example, a papillary muscle or a ventricle wall. The tubular member 140 may be configured to minimize the wear on heart structure caused by relative movement of elongate members 108, 110 and the heart structure to which they may be secured.

Tubular member 140 may include any suitable geometric configuration and dimensions. For example, tubular member 140 may be substantially cylindrical in shape. Tubular member 140 may be made of any suitable biocompatible materials, including, but not limited to, stainless steel. As shown in FIG. 7, tubular member 140 may include a first opening 140a, a second opening 140b, and a lumen 141 extending therebetween. Lumen 141 may be configured to receive an elongate member (e.g., elongate member 108) therein. In some embodiments, the surfaces of lumen 141 may be coated with, for example, a hydrophilic coating to facilitate relative movement between the elongate member received and tubular member 140. In embodiments where elongate members 108, 110 may be secured to a heart wall with an anchoring member, such as, for example, anchor pad 142, the anchoring member may be formed integrally with tubular member 140.

Figure 8A:
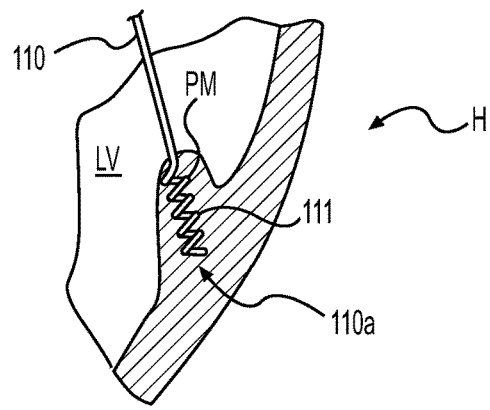
FIGS. 8A-8C depict various heart structure anchoring options, in accordance with embodiments of the present disclosure.
Figure 8B:
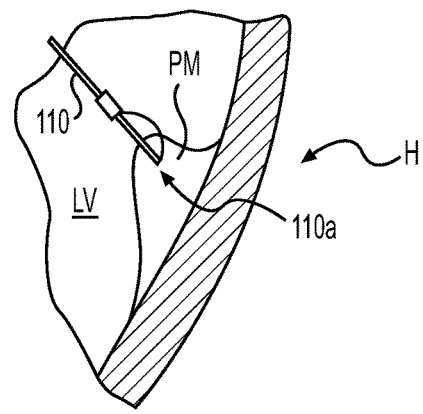
Figure 8C:
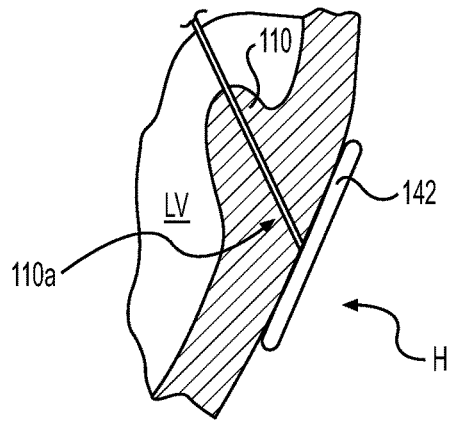

As noted above, ends 108a, 110a may be configured to be secured to heart structure, including, but not limited to, a papillary muscle or a heart wall. Ends 108a, 110a may be secured to heart structure by any suitable manner known in the art that may be configured to allow forces acting on elongate members 108, 110 to pull the heart structure inwards laterally or vertically. In one embodiment, for example, FIG. 8A depicts an end 110a formed as a screw 111, which may be configured to penetrate heart tissue (e.g., a papillary muscle or heart wall) to anchor end 110a to heart tissue. In the exemplary embodiment depicted in FIG. 8B, end 110a may include a loop configured to be sewn through heart structures, such as, for example, the depicted papillary muscle PM. In the exemplary embodiment depicted in FIG. 8C, end 110a may be configured to extend transmurally to an exemplary anchor pad 142. Those of ordinary skill in the art will readily recognize that end 110a of elongate member 110 may be sewn to pad 142 or otherwise mechanically connected thereto. In addition, the principles of the present disclosure contemplate embodiments where anchor pad 142 and end 110a are made of a one-piece construction, which would obviate the need to connect end 110a to pad 142.

Anchor pad 142 may have any suitable geometric configuration and dimension known in the art. In addition, anchor pad 142 may be fabricated from any suitable biocompatible material known in the art. In some embodiments, anchor pad 142 may include any suitable covering or coating known in the art. For example, anchor pad 142 may include a fabric covering configured to promote tissue ingrowth.

With renewed reference to FIGS. 5B and 5C, adjustment mechanism 106 may include any suitable mechanism for adjusting the length and/or the tension in elongate members 108, 110, 112, and 114. As alluded to above, adjusting the length and/or tension of elongate members 108, 110 may alter a shape and or a dimension (e.g., diameter C in FIG. 5A) of body 102, and adjusting the length and/or tension of elongate members 112, 114 may pull laterally and/or vertically the heart structure to which they may be secured. Although the depicted embodiments illustrate a single adjustment mechanism 106 for simultaneously adjusting both a shape or dimension of body 102 and the lengths of elongate members 108, 110, those of ordinary skill in the art will readily recognize that a greater or lesser number of adjustment mechanisms may be provided as desired. In one embodiment, device 100 may be provided with a first adjustment mechanism for adjusting a shape or dimension of body 102 (via elongate members 112, 114), and a second adjustment mechanism for adjusting the lengths/tensions of elongate members 108, 110. In still further embodiments, a single adjustment mechanism 106 may be provided with the capabilities of separately adjusting a shape or dimension of body 102 (via elongate members 112, 114) and the lengths/tensions of elongate members 108, 110.

In one embodiment, adjustment mechanism 106 may include a plurality of pulleys. For example, as shown in FIG. 5C, adjustment mechanism 106 may include a first pulley 120 in-line with a second pulley 122. Although the depicted embodiments indicate that pulley 122 may be disposed on top of pulley 120, those of ordinary skill in the art will readily recognize that first pulley 120 and second pulley 122 may be disposed next to one another. First pulley 120 and second pulley 122 may have any suitable configuration known in the art, and may be made of any suitable material. First pulley 120 and second pulley 122 may be secured to one another or otherwise mechanically connected so that rotation of second pulley 122 results in rotation of first pulley 120, or vice versa. In some embodiments, first pulley 120 and second pulley 122 may have substantially similar configurations and dimensions. In other embodiments, as depicted in FIG. 5C, for example, pulley 120 may have a diameter that is larger than that of pulley 122. The diameters of pulleys 120, 122 may depend on, for example, whether the adjustments caused by rotation of pulleys 120, 122 are configured to be proportional to one another.

As also shown in FIG. 5C, elongate members 112, 114 may be wrapped about pulley 122 so that rotation of pulley 122 may exert forces on ends 104a, 104b via elongate members 112, 114. Similarly, elongate members 108, 110 may be wrapped about pulley 120 so that rotation of pulley 122 may exert forces on the heart structures connected to ends 108a, 110a. Those of ordinary skill in the art will readily recognize that rotating pulleys 120, 122 in a first direction (e.g., clockwise) may cause pulleys 120, 122 to wind in elongate members 108, 110, 112, and 114. Of course, then, rotating pulleys 120, 122 in a second direction (e.g., counterclockwise) may cause pulleys 120, 122 to unwind elongate members 108, 110, 112, and 114.

As alluded to above, pulleys 120, 122 may be rotated simultaneously or separately. In the contemplated embodiments, pulleys 120, 122 may be rotated simultaneously by an actuating mechanism 124. Actuating mechanism 124 may be any mechanism or component suitable for rotating pulleys 120, 122 simultaneously. In one embodiment, actuating mechanism 124 may include a screw-like or otherwise similarly keyed structure disposed perpendicularly to pulleys 120, 122. In another embodiment, actuating mechanism 124 may be disposed in-line with pulleys 120, 122. In further embodiments, actuating mechanism 124 may include an electromechanical actuator (not shown), such as, for example, a nano-motor or a solenoid actuator, configured to rotate pulleys 120, 122. In these embodiments, device 100 may be provided with a suitable power source and a mechanism for selectively activating the electromechanical actuator. For example, device 100 may be provided with a battery and a suitable control device for activating the electromechanical actuator from outside a patient's body. In accordance with the principles of the present disclosure, it is contemplated that providing a control device disposed outside of the patient may facilitate adjustments of device 100 without requiring the patient to undergo (1) repeated surgery or surgery-like procedures and (2) cardiopulmonary bypass.

In embodiments where pulleys 120, 122 are not mechanically connected to one another, actuating mechanism 124 may be connected to both first pulley 120 and second pulley 122. As those of ordinary skill will recognize, actuating mechanism 124 may be configured such that rotation of actuating mechanism 124 may result in rotation of pulleys 120, 122.

Actuating mechanism 124 may be actuated by any suitable manner known in the art. As noted above, for example, a suitable control device (not shown) may be provided to selectively activate embodiments of actuating mechanism 124 that include electromechanical actuators. In other embodiments, however, an actuating tool 126 may be provided to rotate actuating mechanism 124 and pulleys 120, 122. Actuating tool 126 will be discussed in greater detail below.

Although the depicted embodiments indicate that actuating mechanism 124 may be disposed proximate body 102, those of ordinary skill in the art will recognize that actuating mechanism 124 may be appropriately disposed at any suitable, desired location. For example, in one embodiment, actuating mechanism 124 may extend away from the implanted location of device 100, so that adjustments to device 100 may be made from remote locations, including, but not limited to, outside of the patient's heart. In particular, the principles of the present disclosure provide for making adjustments to device 100 from, for example, a subcutaneous pocket disposed in a subclavian region. In such cases, actuating mechanism 124 may extend to the subclavian region.

Actuating tool 126 may be any device suitable for activating actuating mechanism 124 and/or causing rotation of pulleys 120, 122. As shown in FIG. 5B, actuating tool 126 may include a shaft 128 and an end 126a. Shaft 128 may include any geometric configuration and/or dimensions suitable for advancing actuating tool 126 to device 100 within a patient's heart. For example, shaft 128 may include a length that is sufficient to traverse a patient's vasculature so as to be advanced into a patient's heart from outside of the patient's body. In embodiments where actuating mechanism 124 may be a screw or other similarly keyed component, end 126a of actuating tool 126 may include one or more geometric configurations configured to mate with corresponding geometric configurations on actuating mechanism 124, such that rotation of actuating tool 126 results in corresponding rotation of actuating mechanism 124.

In some embodiments, one or more of actuating mechanism 124 and actuating tool 126 may be provided with a feature for providing feedback to an operator. Such feedback may communicate to an operator, for example, the amount of adjustment made to a dimension of body 102 and/or the lengths of elongate members 108, 110. In accordance with one embodiment of the present disclosure, such feedback may be tactile. For example, it is contemplated that as an operator is adjusting one or more aspects of device 100, the operator may experience a series of resistances, wherein each resistance corresponds to a predetermined quantity of adjustment, such as, for example, one (1) millimeter. In other embodiments, the feedback provided to an operator may be audio and/or visual.

In some embodiments, elongate members 108, 110, 112, 114, instead of extending to adjustment mechanism 106, may extend out of and away from body 102. In such embodiments, body 102 may include an extension shaft (not shown) extending perpendicularly away from body 102. The extension shaft may include a lumen within which elongate members 108, 110, 112, 114 may extend through and out of a patient's heart, so as to enable adjustment of device 100 without requiring access to within the patient's heart. For example, elongate members 108, 110, 112, 114, individually or collectively, may be pulled and secured in place from outside of a patient's heart to effect the adjustments described above. The extension shaft may be rigid or flexible, and may be attachable and/or detachable from body 102 as desired. In one embodiment, the extension shaft may be flexible and may extend to a subcutaneous pocket, allowing relatively easy access for adjusting device 100.

Figure 9:
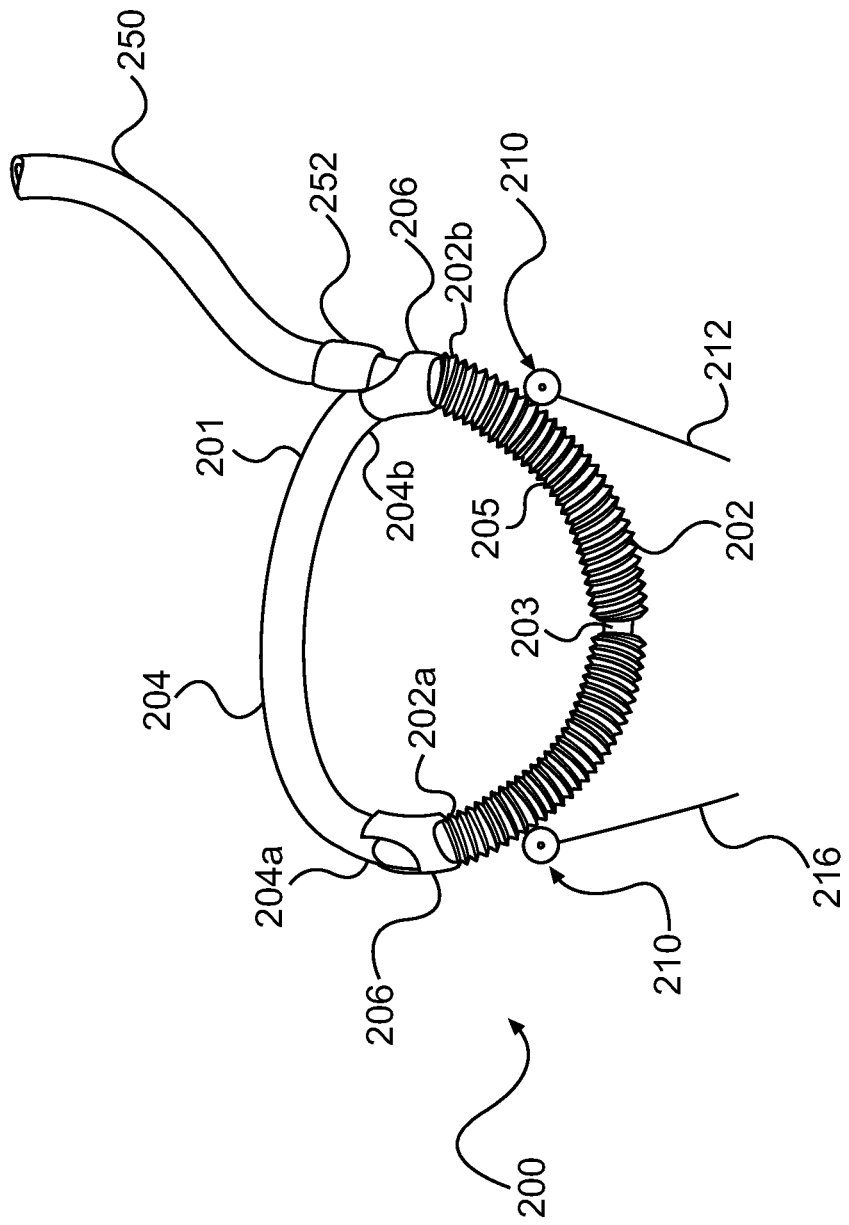
FIG. 9 is a schematic view of a heart treatment device, in accordance with another embodiment of the present disclosure.

Turning now to FIG. 9, there is depicted another embodiment of a heart treatment device 200, in accordance with the principles of the present disclosure. Device 200 may include one or more aspects of device 100 described above. For example, device 200 may comprise a substantially oval-shaped ring 201, and like device 100, a shape or dimension of device 200 may be selectively adjusted. Ring 201 may include a first portion 204 having a first end 204a and a second end 204b. One or both of ends 204a and 204b may include a threaded fastener, such as, for example, a nut, secured thereto. First portion 204 may be substantially similar to body 102 in one or more aspects. For example, first portion 204 may be substantially hollow. In one embodiment, first portion 204 may be relatively rigid so as to afford rigidity to device 200. In other embodiments, first portion 204 may be substantially flexible.

Instead of being adjustable by elongate members 112, 114, and pulley 120, a shape or dimension of device 200 may be adjusted by worm screw 202 having ends 202a, 202b. Although the depicted embodiment indicates that device 200 includes a single worm screw 202, those of ordinary skill in the art will recognize that device 200 may include a greater or lesser number of worm screws. For example, device 200 may include two worm screws (not shown), with each worm screw depending from each of ends 204a, 204b. In embodiments that include a single worm screw 202, one of ends 202a, 202b may be configured to rotate relative to its respective nut 206 without being threaded into or out of nut 206. The embodiment of device 200 depicted in FIG. 9 includes a single worm screw 202. In embodiments that include, for example, two worm screws, however, each worm screw may be rotationally connected to bridging element, such as, for example bridging element 203. Bridging element 203, however, may be utilized with embodiments having a single worm screw 202. In the depicted embodiment, bridging element 203 is disposed approximately between ends 202a, 202b of the depicted worm screw 202.

As shown in FIG. 9, worm screw 202 may include a plurality of external threads 205 about an external surface. External threads 205 may include any suitable configuration and may be configured to correspond with the threads of nut 206, so that end 202b of worm screw 202 may be threaded into its associated nut 206. As will be readily apparent to those of ordinary skill in the art, rotation of worm screw 202 in a first direction relative to nut 206 may cause worm screw 202 to be advanced into nut 206, thereby reducing a dimension (e.g., a diameter and/or a perimeter) of ring 201. Conversely, rotation of worm screw 202 in a second direction relative to nut 206 may cause worm screw 202 to be advanced out of nut 206, thereby increasing a dimension of ring 201.

Rotation of worm screw 202 may be effected by any suitable means known in the art. In one embodiment, an electromechanical actuator, such as, for example, a nanomotor, may be disposed within device 200 for rotation of worm screw 202 relative to nut 206. In another embodiment, a tool 250 may be utilized to mechanically engage and rotate worm screw 202. Tool 250 may be substantially similar to actuating tool 126 in one or more aspects. For example, an end 252 may be configured to mate with an end of worm screw 202 to effect rotation of worm screw 202.

With continued reference to FIG. 9, device 200 may include one or more elongate members 212, 216 depending from device 200 for connection to heart structure, such as, for example, a papillary muscle or a heart wall. Elongate members 212, 216 may be substantially similar to elongate members 108, 110 in one or more aspects Like elongate members 108, 110, a pulling force may be exerted on elongate members 212, 216 to adjust a positioning of the heart structure connected to each of elongate members 212, 216.

To effect simultaneous adjustment of a shape or dimension of ring 201 and exert the aforementioned pulling force on elongate members 212, 216, each of elongate members 212, 216 may be connected to a gear 210. Gear 210 may include any suitable gear mechanism known in the art. As shown in FIG. 10A, gear 210 may include a plurality of surface projections, such as, for example, teeth 210a, which may be configured to be interconnected with threads 205 of worm screw 202. Teeth 210a and threads 205 may interconnected in such as manner so as to cause rotation of gear 210 when worm screw 202 is rotated. As those having ordinary skill in the art will readily appreciate, rotating worm screw 202 in the direction indicated by arrow 230 may cause gear 210 to rotate in the direction indicated by arrow 231, and rotation of gear 210 in the direction indicated by arrow 231 may cause gear 210 to move longitudinally in the direction indicated by arrow 232. As gear 210 moves in the direction indicated by arrow 232, a pulling force may be exerted on the associated elongate member, such as, for example, elongate member 212 and the heart structure to which elongate member 212 may be connected.

Figure 10B:
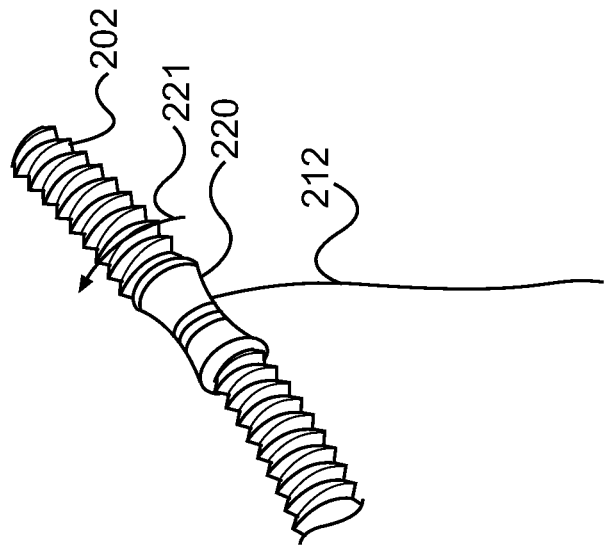
FIGS. 10A-10B depict various configurations of an adjustment component of the heart treatment device of FIG. 9.
Figure 10A:
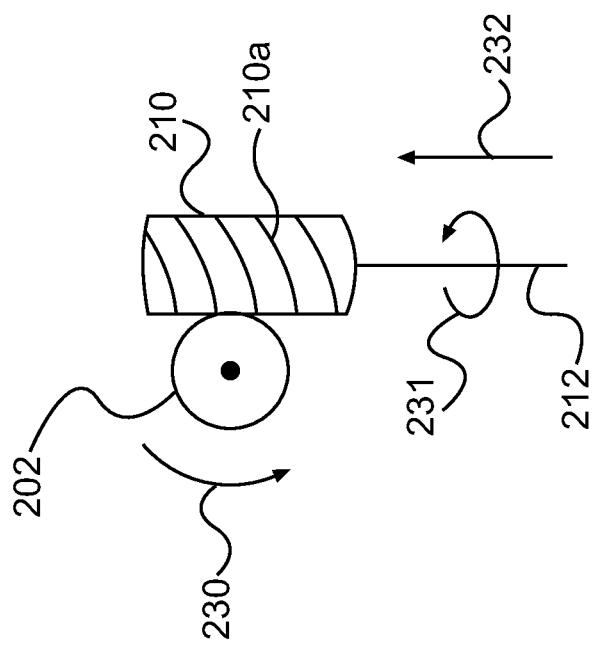

In an alternative embodiment, gear 210 may be replaced by pulley 220, as shown in FIG. 10B. Pulley 220 may include any suitable pulley known in the art. Pulley 220 may be interconnected with worm screw 202 in such a manner so that pulley 220 may rotate when worm screw 202 is rotated. In one embodiment, pulley 220 may form a portion of worm screw 202. In accordance with the principles of the present disclosure, as worm screw 202 and pulley 220 may be rotated in the direction indicated by arrow 221, an elongate member, such as, for example, elongate member 212, may be wound onto pulley 220. As elongate member 212 may be wound onto pulley 220, the length of elongate member 212 extending between pulley 220 and the heart structure to which elongate member 212 may be connected may decrease, thereby increasing a tensile force in elongate member 212, which may lead to pulling the heart structure towards device 200.

Figure 11:
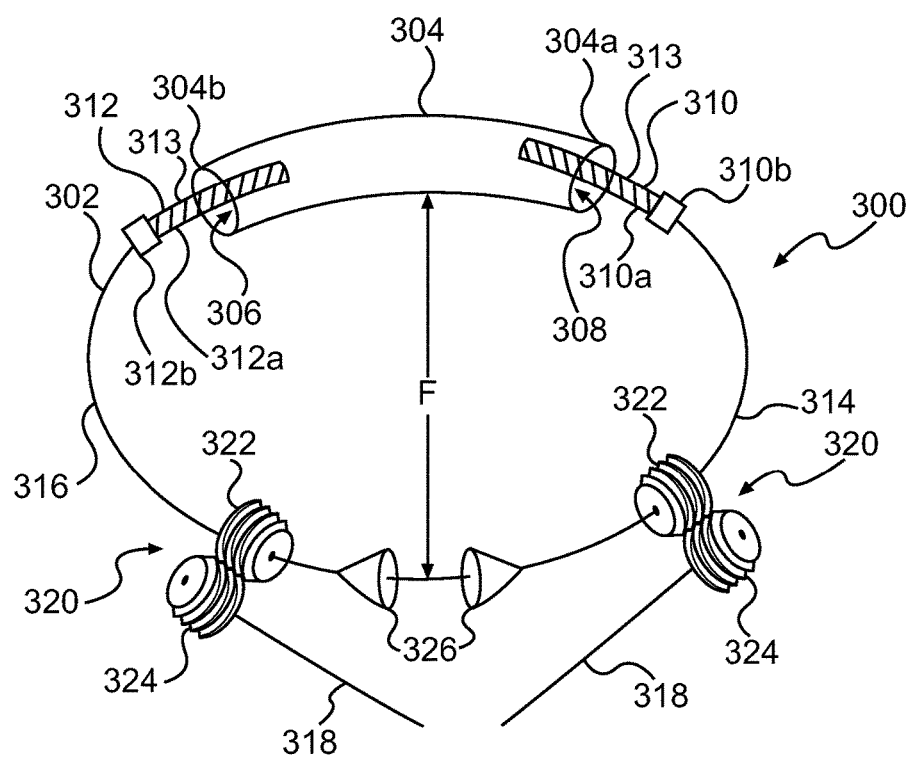
FIG. 11 is a schematic view of a heart treatment device, in accordance with yet another embodiment of the present disclosure.

Turning to FIG. 11, there is depicted yet another embodiment of a heart treatment device 300, in accordance with the present disclosure. Device 300 may include one or more aspects of devices 100 and 200 described above. Device 300 may comprise a ring 302. Ring 302 may include an anterior segment 304 having ends 304a, 304b. Anterior segment 304 may include any suitable geometric configuration and/or dimensions known in the art. For example, anterior segment 304 may comprise a substantially arcuate tube. Ends 304a, 304b may include openings 306, 308, as illustrated in FIG. 11A. Openings 306, 308 may have any suitable configuration and/or dimensions. In one embodiment, openings 306, 308 may be blind openings. In another embodiment, openings 306, 308 may connect within anterior segment 304, thereby creating a lumen within anterior segment 304.

Internal surfaces of openings 306, 308 may be provided with threads (not shown), and openings 306, 308 may be configured to receive threaded fasteners 310, 312, such as, for example, screw-like or otherwise similar fasteners. Threaded fasteners 310, 312 may include shafts 310a, 312a and heads 310b, 312b. Shafts 310a, 312a may be provided with threads 313 configured to mate with the threads of openings 306, 308, so that threaded fasteners 310, 312 may be received within openings 306, 308, respectively. As those with ordinary skill in the art will readily recognize, rotating threaded fasteners 310, 312 in a first direction (e.g., clockwise) may cause threaded fasteners 310, 312 to be advanced into openings 306, 308, respectively. Similarly, rotating threaded fasteners 310, 312 in a second, opposite direction (e.g., counterclockwise) may cause threaded fasteners 310, 312 to be advanced out of openings 306, 308, respectively.

With continued reference to FIG. 11, device 300 may further include an elongate member 314 extending from head 310b of threaded fastener 310. Similarly, an elongate member 316 may extend from head 312b of threaded fastener 312. Elongate members 314, 316 may be integral with heads 310b, 312b or otherwise mechanically connected to heads 310b, 312b so that rotating elongate members 314, 316 may result in corresponding rotation of threaded fasteners 310, 312. In some embodiments, elongate members 314, 316 may include one or more aspects of elongate members 112, 114 described above. Furthermore, elongate members 314, 316 may be joined together at any suitable location, so as to form a ring with anterior segment 304. Alternatively, elongate members 314, 316 may be integral to one another and formed of a one-piece construction. Elongate members 314, 316 may include any suitable configuration known in the art. For example, in some embodiments, elongate members 314, 316 may include a wire or other similar material. In other embodiments, elongate members 314, 316 may be substantially similar to body 102 described above.

Device 300 may further include two or more screw/gear combinations 320. Each of screw/gear combinations 320 may include a gear 322 associated with one of elongate members 314, 316 and a corresponding screw component 324. Each screw component 324 may have one or more elongate members 318 dependent therefrom. Elongate members 318 may be configured for attachment to heart structure, including, but not limited to, a heart wall or papillary muscles. For the purposes of the present disclosure, screw/gear combinations 320 may be substantially similar to the embodiments depicted in FIG. 10A in one or more aspects, such as, for example, operation.

In keeping with the principles of the present disclosure, a shape or dimension of ring 302 may be adjusted by rotating one or both of elongate members 314, 316. In one embodiment, rotation of elongate members 314, 316 may be effected by rotating actuating mechanism 326. As alluded to above, rotation of elongate members 314, 316 may result in corresponding rotation of threaded fasteners 310, 312. As discussed above, rotating threaded fasteners 310, 312 in a first direction may cause threaded fasteners 310, 312 to be threaded into openings 306, 308, thereby reducing the perimeter of ring 302 and decreasing a diameter F. Likewise, rotating threaded fasteners 310, 312 in a second direction may cause threaded fasteners 310, 312 to be threaded out of openings 306, 308, thereby increasing the perimeter of ring 302 and increasing a diameter F. Simultaneously with increasing or decreasing a dimension of ring 302, screw/gear combinations 320 may facilitate altering the positioning of heart geometry via elongate members 318, as previously described in detail with respect to device 100.

As alluded to above, the devices and methods described herein may be applicable to any of the four valves within a patient's heart. Although the embodiments disclosed herein have been discussed relative to a mitral valve MV of a heart, those of ordinary skill in the art will readily recognize that the principles of the present disclosure may be equally applicable to, for example, a tricuspid valve TV.

Figure 12:
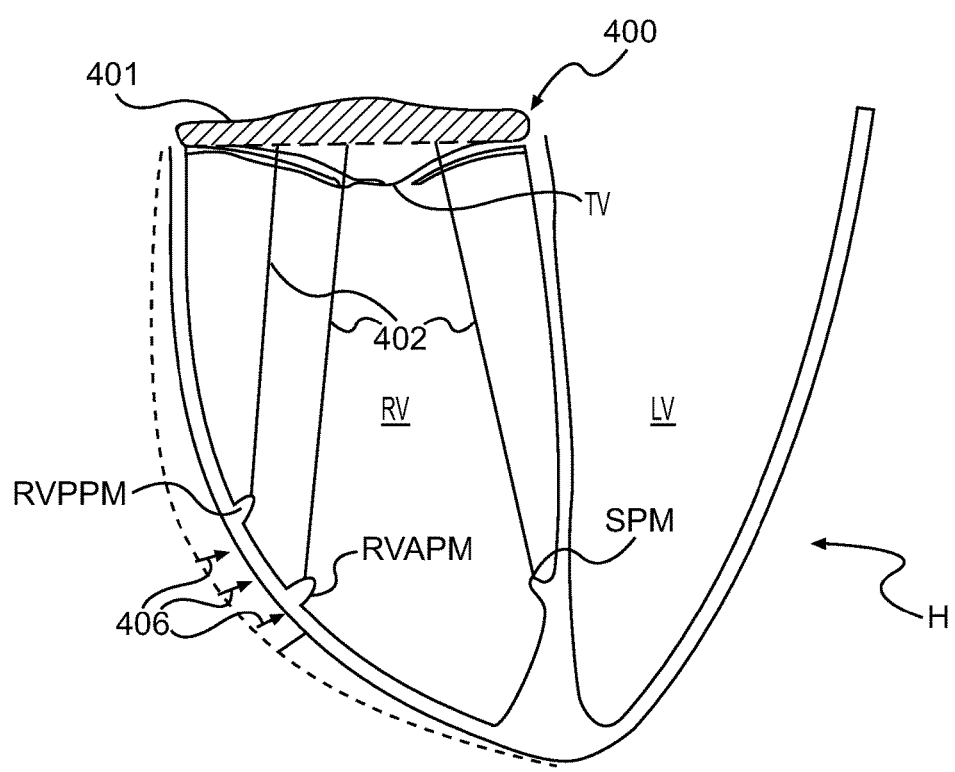
FIG. 12 is a schematic view of a heart treatment device, in accordance with a further embodiment of the present disclosure.

Accordingly, FIG. 12 depicts a schematic of a right ventricle RV and the associated tricuspid valve TV of heart H. In accordance with the principles of the present disclosure, an embodiment of a heart treatment device 400 is also depicted in FIG. 12. Device 400 may include one or more aspects of devices 100, 200, and 300 described above. Device 400, however, may differ in that at least three elongate members 402 may extend from ring 401 for connection to heart structure, including, but not limited to, a heart wall or papillary muscles associated with right ventricle RV. Although the depicted embodiment indicates that elongate members 402 may be secured to the papillary muscles (e.g., septal papillary muscle SPM, anterior papillary muscle RVAPM, and posterior papillary muscle RVPPM) of the right ventricle, those of ordinary skill in the art will readily recognize that one or more of elongate members 402 may be secured to a heart wall, as discussed in connection with device 100. Furthermore, device 400 may be adjustable to, among other things, alter a shape or dimension of ring 401 and adjust the positioning of the heart structure connected to elongate members 402, as previously discussed with respect to device 100. Indeed, as indicated by arrows 406, device 400 may be configured to draw a heart wall HW inwards from the position indicated by dashed lines to the position indicated by solid lines.

With reference to FIGS. 1-12, embodiments of the present disclosure may include methods of treating a heart with the heart treatment devices 100, 200, 300, and/or 400 disclosed herein. As noted above, the devices and methods disclosed herein may be applicable to any heart valve, including, for example, the mitral valve MV and the tricuspid valve TV. In particular, although the embodiments disclosed herein are described relative to the left side of the heart (e.g., the left ventricle LV and the mitral valve MV), those of ordinary skill in the art will readily recognize that the embodiments of the present disclosure may have at least equal applicability to the right side of the heart (e.g., the right ventricle RV and the tricuspid valve TV).

The methods disclosed herein may be performed by any suitable surgical technique known in the art, including, but not limited to, open surgery, minimally invasive or non-invasive surgery, endoscopically, percutaneously, and/or any combination thereof. In one embodiment, it is contemplated that the devices disclosed herein may be implanted within a patient via, for example, a minimally invasive surgical technique known as a thoracotomy, such as, for example, an eight (8) centimeter thoracotomy. In other embodiments, the embodiments described herein may be implanted within a patient's heart via a transapical procedure. In addition, the methods described herein may be performed with or without the aid of cardiopulmonary bypass, as desired. For example, in one embodiment, the devices disclosed herein may be implanted and/or adjusted while heart function has been temporarily ceased and the patient is dependent upon cardiopulmonary bypass (i.e., on-pump). In another embodiment, however, the disclosed devices may be implanted and/or adjusted in accordance with the present disclosure without ceasing heart function (i.e., off-pump).

In one aspect of a method for treating a heart with the devices disclosed herein, a device, such as, for example, device 100, may be advanced to a patient's heart by any suitable methods known in the art. For example, device 100 may be advanced to a treatment site via any standard open-surgery technique. Alternatively, device 100 may be advanced to a treatment site via a transapical approach. Once at the desired treatment site, such as, for example, the mitral valve MV, body 102 may be secured to an atrial side of mitral valve MV. Body 102 may be secured to the annulus of the mitral valve MV by any suitable means known in the art. For example, body 102 may be sewn to the annulus of the mitral valve MV. Next, ends 108a, 110a of elongate members 108, 110 may be brought from the atrial side of the heart to the ventricular side by, for example, piercing the annulus of the mitral valve MV at positions corresponding to the points of exit of elongate members 108, 110. This piercing may be accomplished by any suitable means known in the art. For example, the annulus may be pierced by a surgical tool (not shown) or by needles (not shown) disposed at ends 108a, 110a. Instead of piercing the annulus of mitral valve MV, however, the principles of the present disclosure also provide for simply extending elongate members 108, 110 through mitral valve MV and into left ventricle LV. Once within left ventricle LV, ends 108a, 110a, may be secured to heart structure, such as, for example, the papillary muscles or a heart wall, in accordance with the embodiments described above. In some instances, securing ends 108a, 110a, of elongate members 108, 110 to heart structure may cause elongate members 108, 110 to undergo elongation. For example, the principles of the present invention contemplate an elongation of up to 30% in some embodiments. In other embodiments, the elongation experienced by elongate members 108, 110 may be approximately 5-7%.

Once body 102 and elongate members 108, 110 have been appropriately secured, the heart may be surgically closed, its cavities evacuated from air and allowed to fill with blood, and normal heart rhythm may be resumed. Stated differently, the patient may be taken off of cardiopulmonary bypass. Subsequently, under guidance afforded by any suitable imaging technique, such as, for example, transesophageal echocardiography, actuating tool 126 may be advanced to adjustment mechanism 124 for adjusting one or more aspects of device 100, so as to improve heart function and, specifically, valve function. To facilitate suitable imaging, those of ordinary skill in the art will recognize that the embodiments disclosed herein may be provided with one or more appropriately located visible markers, such as, for example, radiopaque markers.

In particular, the principles of the present disclosure provide for reducing diameter C of device 100 and, consequently, the annulus of the valve it is attached to, by approximately twenty-four (24) to approximately forty-two (42) millimeters. In addition, the posterior papillary muscle LVPPM may be drawn inwards laterally and/or vertically by approximately thirty (30) millimeters. The anterior papillary muscle LVAPM may be drawn inwards laterally and/or vertically by approximately ten (10) millimeters. Finally, the lengths of elongate members 108, 110 may be adjusted to be between approximately fifteen (15) to thirty (30) millimeters. As a result of one or more of these adjustments, the papillary muscles LVAPM, LVPPM may be drawn closer together by approximately twenty (20) millimeters. Further, a shape of body 102 may be altered. For example, body 102 may be caused to bow upwards by approximately thirty (30) degrees out of the plane of the mitral valve. As those of ordinary skill in the art will readily recognize, all of these adjustments may be made simultaneously by, for example, rotating actuating mechanism 124 with actuating tool 126. In accordance with the principles of the present disclosure, adjusting device 100 in the aforementioned manner while the heart is beating may afford an operator the opportunity to identify improper heart valve function and finely tune device 100 to address inaccuracies not otherwise addressable by non-adjustable heart treatment devices.

The aforementioned adjustments to device 100 may be made at any suitable time. For example, device 100 may be adjusted during an implantation procedure. In addition, or alternatively, device 100 may be adjusted shortly after implantation, such as, for example, between two (2) to ten (10) days after implantation. Furthermore, device 100 may be adjusted again at any time necessary, such as, for example, six (6) months or one (1) year after implantation.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for treating a heart, comprising:
an elongated curvilinear body comprising an annuloplasty ring having structure that facilitates attachment to the atrioventricular heart valve annulus, the body having a shape that conforms around at least a portion of an atrioventricular heart valve annulus and is configured to be secured thereto, the body defining an atrial side opposite a ventricular side;
a flexible first elongated member engaged by and extending from an adjustment mechanism through a channel that extends within and around a length of the body and out of an opening in the body on the ventricular side thereof, wherein an end of the first elongate member is configured to be secured to heart geometry in the ventricle, the adjustment mechanism being configured to alter a length or tension of the first elongate member and thus alter a distance between the body and the end of the first elongate member that is secured to the heart geometry; and
a flexible second elongated member engaged by and extending from the adjustment mechanism through the channel in the body and connected to a portion of the body, the adjustment mechanism being configured to alter a length or tension of the second elongate member and thus alter the shape or dimension of the body, and wherein
wherein the adjustment mechanism includes a component configured for rotation and accessible from the atrial side of the body, wherein the first and second elongated members pass around a pulley located within the body and rotated by the component.

2. The device of claim 1, wherein the structure that facilitates attachment to the atrioventricular heart valve annulus comprises a covering around the body configured to promote tissue ingrowth.

3. The device of claim 1, wherein the end of the first elongate member configured to be secured to heart geometry in the ventricle includes a tissue anchor.

4. The device of claim 3, wherein the tissue anchor includes a loop configured to be sewn through the heart geometry in the ventricle.

5. The device of claim 1, wherein the adjustment mechanism comprises a first pulley and a second pulley that are mechanically connected so that rotation of one pulley results in rotation of the other pulley, and vice versa, and the first pulley has a diameter different than that of the second pulley, and wherein the flexible first elongated member extends around the first pulley and the flexible second elongated member extends around the second pulley.

6. The device of claim 1, further including a stiffener provided in the channel in the body and wherein there are two flexible second elongated members each engaged by and extending in opposite directions from the adjustment mechanism through the channel and connected to opposite ends of the stiffening member.

7. The device of claim 6, wherein the stiffener comprises a plurality of spaced-apart segments.

8. The device of claim 1, wherein there are two of the first elongated members each engaged by and extending in opposite directions from the adjustment mechanism around a length of the body and out of different openings in the body on the ventricular side thereof.

9. A device for treating a heart, comprising:
an elongated curvilinear body comprising an annuloplasty ring having structure that facilitates attachment to the annuloplasty ring to the atrioventricular heart valve annulus, the body having a shape that conforms around at least a portion of an atrioventricular heart valve annulus and is configured to be secured thereto, the body defining an atrial side opposite a ventricular side, the body further defining internal channels extending around a circumference thereof and a stiffening member on one side of the body, the stiffening member having opposite ends in communication with the channels, the body housing an adjustment mechanism also open to the channels;
a flexible first elongated member engaged by and extending from the adjustment mechanism through one of the channels and out of an opening in the body on the ventricular side thereof, wherein an end of the first elongate member is configured to be secured to a papillary muscle in the ventricle; and
two flexible second elongated members each engaged by and extending in opposite directions from the adjustment mechanism through the channels and connected to opposite ends of the stiffening member, and wherein
actuation of the adjustment mechanism simultaneously changes a length or tension of the first elongate member to alter a distance between the body and papillary muscle in the ventricle and changes a length or tension of the second elongate members and thus alters a shape or dimension of the body, wherein the adjustment mechanism includes a component configured for rotation and accessible from the atrial side of the body.

10. The device of claim 9, wherein the structure that facilitates attachment to the atrioventricular heart valve annulus comprises a covering around the body configured to promote tissue ingrowth.

11. The device of claim 9, wherein the end of the first elongate member configured to be secured to a papillary muscle in the ventricle includes a tissue anchor.

12. The device of claim 11, wherein the tissue anchor includes a loop configured to be sewn through the papillary muscle.

13. The device of claim 9, wherein the adjustment mechanism comprises a first pulley and a second pulley that are mechanically connected so that rotation of one pulley results in rotation of the other pulley, and vice versa, and the first pulley has a diameter different than that of the second pulley, and wherein the flexible first elongated member extends around the first pulley and the two flexible second elongated members extend around the second pulley.

14. The device of claim 9, wherein there are two of the first elongated members each engaged by and extending in opposite directions from the adjustment mechanism through the channels and out of different openings in the body on the ventricular side thereof.

15. A device for treating a heart, comprising:
an elongated curvilinear body comprising an annuloplasty ring having structure that facilitates attachment to the annuloplasty ring to the atrioventricular heart valve annulus, the body having a shape that conforms around at least a portion of an atrioventricular heart valve annulus and is configured to be secured thereto, the body defining an atrial side opposite a ventricular side, the body further being flexible and having a hollow interior space within which is located an adjustment mechanism;
a flexible first elongated member engaged by and extending from the adjustment mechanism around a length of the body and out of an opening in the body on the ventricular side thereof, wherein an end of the first elongate member is configured to be secured to heart geometry in the ventricle; and
a flexible second elongated member engaged by and extending from the adjustment mechanism around a length of the body and connected to a point on the body, and wherein
actuation of the adjustment mechanism simultaneously changes a length or tension of the first elongate member to alter a distance between the body and heart geometry in the ventricle, as well as changes a length or tension of the second elongate member to alter a shape or dimension of the body by flexing, wherein the adjustment mechanism includes a component configured for rotation and accessible from the atrial side of the body, wherein the first and second elongated members passes around a pulley located within the body and rotated by the component.

16. The device of claim 15, wherein the structure that facilitates attachment to the atrioventricular heart valve annulus comprises a covering around the body configured to promote tissue ingrowth s.

17. The device of claim 15, wherein the end of the first elongate member configured to be secured to heart geometry in the ventricle includes a tissue anchor.

18. The device of claim 17, wherein the tissue anchor includes a loop configured to be sewn through the heart geometry in the ventricle.

19. The device of claim 15, wherein the adjustment mechanism comprises a first pulley and a second pulley that are mechanically connected so that rotation of one pulley results in rotation of the other pulley, and vice versa, and the first pulley has a diameter different than that of the second pulley, and wherein the flexible first elongated member extends around the first pulley and the flexible second elongated member extends around the second pulley.

20. The device of claim 15, wherein there are two of the first elongated members each engaged by and extending in opposite directions from the adjustment mechanism through the hollow interior space and out of different openings in the body on the ventricular side thereof, and two of the flexible second elongated members each engaged by and extending in opposite directions from the adjustment mechanism through the hollow interior space and connected to different points on the body.

\* \* \* \* \*